United States Patent
Atkinson et al.

(10) Patent No.: US 7,562,587 B2
(45) Date of Patent: Jul. 21, 2009

(54) DETERMINATION OF DENSITY FOR METERING A FLUID FLOW

(75) Inventors: Ian Atkinson, Ely (GB); John Sherwood, Cambridge (GB)

(73) Assignee: Schlumberger Technology Corporation, Cambridge, MA (US)

( * ) Notice: Subject to any disclaimer, the term of this patent is extended or adjusted under 35 U.S.C. 154(b) by 0 days.

(21) Appl. No.: 12/048,774

(22) Filed: Mar. 14, 2008

(65) Prior Publication Data

US 2009/0114038 A1    May 7, 2009

(30) Foreign Application Priority Data

Nov. 3, 2007    (GB) ................... 0721636.9

(51) Int. Cl.
*G01F 1/44* (2006.01)
(52) U.S. Cl. .................................. 73/861.63
(58) Field of Classification Search .............. 73/861.63, 73/861.04, 861.52, 861.64
See application file for complete search history.

(56) References Cited

U.S. PATENT DOCUMENTS

| | | | | |
|---|---|---|---|---|
| 4,232,549 | A | * | 11/1980 | Migrin et al. ................... 73/202 |
| 4,282,751 | A | * | 8/1981 | Brown et al. ................... 73/202 |
| 4,467,659 | A | | 8/1984 | Baumoel |
| 5,007,293 | A | | 4/1991 | Jung |
| 5,203,211 | A | | 4/1993 | Jung |
| 5,251,490 | A | | 10/1993 | Kronberg |
| 5,400,657 | A | | 3/1995 | Kolpak et al. |
| 5,463,906 | A | | 11/1995 | Spani et al. |
| 5,693,891 | A | * | 12/1997 | Brown et al. .............. 73/861.04 |
| 5,793,216 | A | | 8/1998 | Constant |
| 5,905,208 | A | | 5/1999 | Ortiz et al. |
| 6,058,787 | A | * | 5/2000 | Hughes ................... 73/861.63 |
| 6,575,043 | B1 | | 6/2003 | Huang et al. |
| 6,622,574 | B2 | * | 9/2003 | Fincke ..................... 73/861.63 |
| 6,758,100 | B2 | | 7/2004 | Huang |

(Continued)

FOREIGN PATENT DOCUMENTS

GB    2177803 A    1/1987

(Continued)

OTHER PUBLICATIONS

U.S. Appl. No. 12/048,831, Ian Atkinson filed Mar. 14, 2008.*

(Continued)

*Primary Examiner*—Jewel Thompson
(74) *Attorney, Agent, or Firm*—James McAleenan; Steven Gahlings; Michael Ford

(57) ABSTRACT

Systems and methods are disclosed for measuring densities and flow rates of gas-liquid fluid mixtures. In the systems and methods, the fluid mixture is caused to exhibit swirling flow as it flows through a conduit that includes a constriction, a first pressure difference is measured between two vertically-spaced measurement positions in the conduit, a second pressure difference is measured between two horizontally-spaced measurement positions in the conduit, the first horizontally-spaced measurement position being at the constriction region and the second horizontally-spaced measurement position being upstream or downstream of the constriction region, and one or more of the pressure differences is used to determine a density or a flow rate of the gas-liquid fluid mixture.

18 Claims, 3 Drawing Sheets

U.S. PATENT DOCUMENTS 6,831,470 B2  12/2004  Xie et al.
7,327,146 B2   2/2008  Simon

FOREIGN PATENT DOCUMENTS

| | | |
|---|---|---|
| GB | 2279146 A | 12/1994 |
| GB | 2343249 A | 5/2000 |
| GB | 2343249 B | 1/2001 |
| GB | 2363455 A | 12/2001 |
| GB | 2359435 B | 5/2002 |
| GB | 2363455 B | 10/2002 |
| GB | 2376074 A | 12/2002 |
| GB | 2406386 A | 3/2005 |
| GB | 2420299 A | 5/2006 |
| WO | 95/33980 A1 | 12/1995 |
| WO | 00/03207 A1 | 1/2000 |
| WO | 2004106861 A2 | 12/2004 |
| WO | 2005031311 A1 | 4/2005 |

OTHER PUBLICATIONS

Atkinson et al: "New generation multiphase flowmeters from Schlumberger and Framo Engineering AS", 17th International North Sea Flow Measurement Workshop, Oslo, Norway, Oct. 25-28, 1999.

Batchelor: "Steady axisymmetric flow with swirl", An Introduction to Fluid Dynamics, Cambridge University Press, 2000, section 7.5, pp. 543-555.

Clark: "Liquid film thickness measurement", Multiphase Science and Technology, vol. 14, No. 1, 2002, pp. 1-74.

Constant et al: "Multiphase metering using ultrasonics as an alternative approach", Documentation of Multiphase Metering Conference, Mar. 12-13, 1997, The Airport Skean Hotel, Aberdeen, Organised by IBC Technical Services Ltd.

Falcone et al: "ANUMET—a novel wet gas flowmeter", SPE Annual Technical Conference and Exhibition, Denver, Colorado, Oct. 5-8, 2003, SPE 84504.

FolgerØ et al: "Permittivity measurement of thin liquid layers using open-ended coaxial probes", Measurement Science and Technology, vol. 7, 1996, pp. 1164-1173.

Gibson et al: "Keynote paper—Swirling flow through Venturi tubes of convergent angle 10.5° and 21°", Proceedings of FEDSM2006, 2006 ASME Joint U.S.—European Fluids Engineering Summer Meeting, Miami, Florida, Jul. 17-20, 2006, FEDSM2006-98229.

Greenwood et al: "Self-calibrating sensor for measuring density through stainless steel pipeline wall", Journal of Fluids Engineering, vol. 126, 2004, pp. 189-192.

Gudmundsson et al: "Gas-liquid metering using pressure-pulse technology", SPE Annual Technical Conference and Exhibition, Houston, Texas, Oct. 3-6, 1999, SPE 56584.

Gunarathne et al: "Novel techniques for monitoring and enhancing dissolution of mineral deposits in petroleum pipelines", Offshore Europe Conference, Aberdeen, Sep. 5-8, 1995, SPE 30418.

Hammer: "Flow permittivity models and their application in multiphase meters", Proceedings of Multiphase Metering, IBC Technical Services, Aberdeen Mar. 12-13, 1997.

Hayman et al: "High-resolution cementation and corrosion imaging by ultrasound", SPWLA 32nd Annual Logging Symposium, Midland, TX, USA, Jun. 16-19, 1991, paper KK.

Lynnworth: "Level of liquids and solids", Ultrasonic measurements for process control. Theory, techniques, applications, Academic Press, 1989, chapter 2, section 2.4.3, pp. 58-63.

Lynnworth: "Ultrasonic measurements for process control. Theory, techniques, applications", Academic Press, 1989, pp. 23-27, 30, 32-35, 254-255, 312-317.

Takeda: "Velocity profile measurement by ultrasound Doppler shift method", Int. J. Heat & Fluid Flow, vol. 7, No. 4, 1986, pp. 313-318.

Theron et al: "Stratified flow model and interpretation in horizontal wells", SPE Annual Technical Conference and Exhibition, Denver, Colorado, Oct. 6-9, 1996, SPE 36560.

Willemetz et al: "Instantaneous Doppler frequency measurement and implementation in a multigate flowmeter", EUROSON 87, Helsinki, Finland, Jun. 14-18, 1987.

XIE: "Measurement of multiphase flow water fraction and water-cut", American Institute of Physics Conference Proceedings, Jun. 5, 2007, vol. 914, pp. 232-239. Proc. 5th Int. Symp. on Measurement Techniques for Multiphase Flows (5th ISMTMF), Dec. 11-14, 2006, Macau, China.

* cited by examiner

DETERMINATION OF DENSITY FOR METERING A FLUID FLOW

CROSS-REFERENCE TO RELATED APPLICATIONS

The present application claims priority under 35 U.S.C. §119 to Great Britain Application No. 0721636.9, filed on Nov. 3, 2007, naming Atkinson et al. as inventors, which is incorporated herein by reference in its entirety for all purposes.

FIELD OF THE INVENTION

The present invention relates to a method of measuring the density of fluid flow, and more particularly to a method of measuring the flow rate of a gas-liquid fluid mixture.

BACKGROUND OF THE INVENTION

The determination of gas and liquid flow rates and mixture densities in gas-liquid fluid mixtures is important in the oil and gas industry.

An example of an apparatus for measuring such flow rates is Schlumberger's Vx™ system (see e.g. I. Atkinson, M. Berard, B.-V. Hanssen, G. Ségéral, $17^{th}$ International North Sea Flow Measurement Workshop, Oslo, Norway 25-28 October 1999 "New Generation Multiphase Flowmeters from Schlumberger and Framo Engineering AS") which comprises a vertically mounted Venturi flow meter, a dual energy gamma-ray hold up measuring device and associated processors. This system allows the simultaneous calculation of gas, water and oil volumetric flow rates in multi phase flows.

Although providing proven performance, the Vx™ system and other conventional multiphase flow meters are relatively expensive, which tends to preclude their application in "brown" field sites (i.e. oil and gas wells where capacity has fallen below about 1000 barrels/day (0.0018 m$^3$/sec)) and other low hydrocarbon producers. However, such sites probably account for around 2-3 million oil and gas wells worldwide.

SUMMARY OF THE INVENTION

The present invention is at least partly based on the realisation that it is possible to measure a vertical pressure difference across a substantially horizontally conduit conveying a fluid flow, and to use that pressure difference to determine the fluid density. The fluid density can then be used to calculate a flow rate, such as the liquid or the gas flow rate in the flow of a gas-liquid fluid mixture, or for other purposes.

Thus, in general terms, the present invention provides a method and a corresponding apparatus for determining the density of a fluid, such as a gas-liquid fluid mixture.

A first aspect of the present invention provides a method for measuring the density of a fluid including the steps of:
  providing a conduit through which the fluid (such as a gas-liquid fluid mixture) flows, the conduit extending substantially horizontally;
  measuring a pressure difference between two vertically-spaced measurement positions in the conduit (e.g. at facing upper and lower wall portions of the conduit); and
  using the pressure difference to determine the density of the fluid.

Measuring the pressure difference in a direction perpendicular to the flow direction has an advantage in that the frictional pressure loss caused by the measurement will generally be zero. Frictional pressure losses can be difficult to predict, in particular for multiphase flows, and can introduce significant errors in density measurements.

Density is an important parameter in process control. In multiphase flow it can be used (along with the known or measured single phase densities) to determine the fractional hold up. This is important if the flow proceeds e.g. to a device that can only handle a certain gas fraction, such as a pump.

However, more particularly, this aspect of the present invention provides a method for measuring a flow rate of a gas-liquid fluid mixture including the steps of:
  providing a conduit through which the gas-liquid fluid mixture flows, the conduit extending substantially horizontally and having a constriction region having a reduced conduit cross-section;
  measuring a first pressure difference between two vertically-spaced measurement positions in the conduit;
  measuring a second pressure difference between two horizontally-spaced measurement positions in the conduit, the first horizontally-spaced measurement position being at the constriction region and the second horizontally-spaced measurement position being upstream or downstream of the constriction region; and
  using the first and the second pressure differences to determine a flow rate (such as the gas flow rate and/or the liquid flow rate) of the gas-liquid fluid mixture. Thus the first pressure difference of the method for measuring a flow rate corresponds to the pressure difference of the more general method for measuring the density of a fluid. Typically, and conveniently, the vertically-spaced measurement positions can be on a conduit transverse cross-section which also contains one of the horizontally-spaced measurement positions. In this case, that horizontally-spaced measurement position can coincide with one of the vertically-spaced measurement positions.

Unlike the Vx™ system, which requires gamma-ray-determined hold-ups to calculate flow rates, the method for measuring a flow rate uses the first pressure difference (which is effectively a measurement of the mixture density or gravitational pressure head across the conduit) in the determination of flow rates. As a pressure difference measurement can be obtained using relatively inexpensive, conventional and robust technology, a multiphase flow meter that applies the method may be suitable for use in brown field sites. A further advantage relative to the Vx™ system is that health and safety issues pertaining to the use of gamma-ray sources can be avoided.

In general, in order to calculate a fluid density from the first pressure difference, and also to calculate a flow rate using that density and the second pressure difference, the fluid mixture should exhibit a predetermined type of flow at the measurement positions. For example, if it is known that the mixture is e.g. stratified, churning, or homogenised, appropriate adjustments can be made to relations used in the calculation of the fluid density and flow rate. Preferably, however, the mixture is conditioned to exhibit swirling flow, which separates the liquid from the gas at the measurement positions. For example, the conduit may have a swirl element, such as a helical insert or vane assembly, for inducing the mixture to exhibit swirling flow at these positions. The swirl element may include one or more spiral-shaped members extending along the conduit in the direction of fluid flow. Preferably, the spiral shaped members are positioned at the wall of the conduit and, when viewed along the axis the conduit, leave a central core of the conduit unimpeded (i.e. they do not extend radially inwards as far as the central axis of the conduit). Alternatively, the swirl element may be formed by a tangential flow inlet to the conduit.

An advantage of swirling flow is that it is relatively easy to induce and sustain (unlike stratified or homogenised flow which may be unstable over typical measurement distances). Further, modelling the characteristics of swirling flow through a Venturi is relatively straightforward, compared to e.g. modelling stratified or churning flow. Also, swirling flow is symmetrical about the flow axis, resulting in the second pressure difference being independent of angular orientation.

Inducing the mixture to exhibit swirling flow separates the liquid and gas phases of the mixture. The swirling flow causes the liquid of the mixture to be displaced to the wall of the conduit, e.g. to form an annulus of liquid adjacent the wall of the conduit, leaving a gas core at the centre of the conduit.

Swirling flow in the constriction region will have increased centrifugal acceleration relative to swirling flow outside the constriction region (e.g. at the entrance to the constriction region). This increased centrifugal acceleration can enhance the displacement of liquid to the wall of the conduit. Thus preferably, the swirling flow in the constriction region is induced by provoking swirling flow in the conduit upstream of the constriction region.

Within the constriction region, the separated liquid layer tends to flow more slowly than the gas, which increases the liquid hold up, making it easier to investigate the properties of the liquid. Further, enhanced centrifugal separation at the constriction region can reduce the amount of entrained gas in the liquid, improving estimates of gas or liquid hold-up.

The second horizontally-spaced measurement position is preferably upstream of the constriction region. When the mixture is conditioned to exhibit swirling flow in the conduit upstream of the constriction region, the second horizontally-spaced measurement position can be within that swirling flow.

Typically, the constriction region is provided by a Venturi. The constriction region may be the throat of the Venturi. The second horizontally-spaced measurement position can be at the inlet to the Venturi.

The method may further include the step of measuring the absolute pressure of the flow, e.g. at one of the measurement positions, but preferably on a transverse cross-section of the conduit containing the vertically-spaced measurement positions. The absolute pressure may also then be used in the determination of the flow rate. The method may further include the step of measuring the temperature of the flow e.g. at one of the measurement positions, but preferably on the transverse cross-section of the conduit containing the vertically-spaced measurement positions. The temperature may also be used in the determination of the flow rate.

The method may further including the step of measuring a third pressure difference between two further vertically-spaced measurement positions in the conduit (e.g. at facing upper and lower wall portions of the conduit) spaced upstream or downstream of the vertically-spaced measurement positions where the first pressure difference is measured;

wherein the first, second and third pressure differences are used to determine said flow rate. Typically, and conveniently, the further vertically-spaced measurement positions can be on a conduit transverse cross-section which also contains one of the horizontally-spaced measurement positions. In particular, when the vertically-spaced measurement positions for the first pressure difference are on a conduit transverse cross-section which contains one of the horizontally-spaced measurement positions, the further vertically-spaced measurement positions for the third pressure difference can be on a conduit transverse cross-section which contains the other of the horizontally-spaced measurement positions. In this case, that other horizontally-spaced measurement position can coincide with one of the further vertically-spaced measurement positions.

The third pressure difference, which like the first pressure difference is effectively the measurement of the mixture density or gravitational pressure head across the conduit, can be used to compensate for slip in the flow of the mixture when determining the flow rate.

To compensate for irregularities in the flow and to reduce the effect of noise in the measurements, the measured pressure difference(s) may be time-averaged pressure difference(s).

The method may further include the step of measuring the absolute pressure of the flow on a transverse cross-section of the conduit containing the further vertically-spaced measurement positions and preferably at one of the further vertically-spaced measurement positions, wherein this absolute pressure is also used in the determination of the flow rate. The method may further include the step of measuring the temperature of the flow on the transverse cross-section of the conduit containing the further vertically-spaced measurement positions and preferably at one of the further vertically-spaced measurement positions, wherein this temperature is also used in the determination of the flow rate.

The liquid of the mixture may comprise oil and/or water. The gas may comprise natural gas. Thus the gas-liquid fluid mixture may be a mixture of natural gas, condensate and optionally water.

A second aspect of the present invention provides an apparatus for providing measurements useable in determining the density of a fluid, the apparatus including:

a conduit through which the fluid (such as a gas-liquid fluid mixture) can flow, the conduit extending substantially horizontally; and a pressure meter for measuring a pressure difference between two vertically-spaced measurement positions (e.g. at facing upper and lower wall portions of the conduit) in the conduit;

wherein the pressure difference is usable to determine the density of the fluid.

More particularly, the second aspect of the present invention provides an apparatus for providing measurements useable in determining a flow rate of a gas-liquid fluid mixture, the apparatus including:

a conduit through which the gas-liquid fluid mixture can flow, the conduit extending substantially horizontally and having a constriction region having a reduced conduit cross-section;

a first pressure meter for measuring a first pressure difference between two vertically-spaced measurement positions in the conduit; and a second pressure meter for measuring a second pressure difference between two horizontally-spaced measurement positions in the conduit, the first horizontally-spaced measurement position being at the constriction region and the second horizontally-spaced measurement position being upstream or downstream of the constriction region;

wherein the first and the second pressure differences are usable to determine a flow rate (such as the gas flow rate and/or the liquid flow rate) of the gas-liquid fluid mixture. Thus the first pressure meter of the method for providing measurements useable in determining a flow rate corresponds to the pressure meter of the more general method for providing measurements useable in determining the density of a fluid. The vertically-spaced measurement positions may be on a conduit transverse cross-section which also contains one of the horizontally-spaced measurement positions. In this case, that horizontally-spaced measurement position can coincide with one of the vertically-spaced measurement positions.

Thus the apparatus can be used in the performance of the method of the first aspect. Optional features of the first aspect may therefore be applied to the second aspect.

For example, the apparatus may further include a conditioning element which conditions the fluid mixture to exhibit a predetermined type of flow at the measurement positions. The conditioning element may be a swirl element for inducing the mixture to exhibit swirling flow at the measurement positions. The swirl element may include one or more spiral-shaped members extending along the conduit in the direction of fluid flow.

The second horizontally-spaced measurement position may be upstream of the constriction region.

The constriction region may be provided by a Venturi. The constriction region may be the throat of the Venturi. The second horizontally-spaced measurement position may be at the inlet to the Venturi.

The apparatus may further include a device for measuring the absolute pressure of the flow, e.g. at one of the measurement positions, but preferably on a transverse cross-section of the conduit containing the vertically-spaced measurement positions (conveniently this device can be incorporated in the first pressure meter itself). The apparatus may further include a device for measuring the temperature of the flow e.g. at one of the measurement positions, but preferably on the transverse cross-section of the conduit containing the vertically-spaced measurement positions.

The apparatus may further include a third pressure meter for measuring a third pressure difference between two further vertically-spaced measurement positions in the conduit (e.g. at facing upper and lower wall portions of the conduit) spaced upstream or downstream of the vertically-spaced measurement positions where the first pressure difference is measured. The further vertically-spaced measurement positions can be on a conduit transverse cross-section which also contains one of the horizontally-spaced measurement positions. In particular, when the vertically-spaced measurement positions for the first pressure difference are on a conduit transverse cross-section which contains one of the horizontally-spaced measurement positions, the further vertically-spaced measurement positions for the third pressure difference can be on a conduit transverse cross-section which contains the other of the horizontally-spaced measurement positions. In this case, that other horizontally-spaced measurement position can coincide with one of the further vertically-spaced measurement positions.

The pressure meter(s) may measure time-averaged pressure differences.

The apparatus may further include a device for measuring the absolute pressure of the flow on a transverse cross-section of the conduit containing the further vertically-spaced measurement positions and preferably at one of the further vertically-spaced measurement positions (conveniently this device can be incorporated in the third pressure meter itself). The apparatus may further include a device for measuring the temperature of the flow on the transverse cross-section of the conduit containing the further vertically-spaced measurement positions and preferably at one of the further vertically-spaced measurement positions.

A third aspect of the present invention provides a meter (e.g. a densitometer or a hold up meter) including the apparatus for providing measurements useable in determining the density of a fluid of the second aspect, and a processor arranged to determine a density of the fluid using the pressure difference measured by the pressure meter of the apparatus.

More particularly, the third aspect of the invention provides a flow meter including the apparatus for providing measurements useable in determining a flow rate of a gas-liquid fluid mixture of the second aspect, and a processor arranged to determine a flow rate of the gas-liquid fluid mixture using the pressure differences measured by the pressure meters of the apparatus (and optionally the or each measured absolute pressure and/or the or each measured temperature).

The processor may calculate respective time-averaged pressure difference(s) from sequences of pressure differences measured by the pressure meter(s), the time-averaged pressure difference(s) then being used to determine the density or the flow rate.

A further aspect of the present invention provides an oil well pipeline or a gas well pipeline including an apparatus according to the second aspect or a meter according to the third aspect.

A further aspect of the present invention provides an apparatus according to the second aspect when conveying a gas-liquid fluid mixture, or a meter according to the third aspect when conveying a gas-liquid fluid mixture.

Another aspect of the present invention provides a section of conduit having a conduit wall and having upper and lower fluid passages which each traverse the wall;
  wherein each fluid passage extends between an inner opening on the internal face of the wall and an outer opening on the external face of the wall, and the passages are arranged such that, when the section of conduit is viewed along its axial direction with the inner opening of the upper passage directly above the inner opening of the lower passage, the passages extend substantially horizontally between their respective inner and outer openings.

Thus the section of conduit may be part of the conduit of the first or second aspect, the inner openings of the fluid passages providing the vertically-spaced measurement positions at which the first pressure difference is measured, or the further vertically-spaced positions at which the third pressure difference is measured.

In use, the section of conduit will be arranged with the inner opening of the upper passage vertically above the inner opening of the lower passage. Because the passages will then extend substantially horizontally across the wall of the conduit section between their respective inner and outer openings, unnecessary fluid columns above the inner opening of the upper passage and below the inner opening of the lower passage can be avoided. This in turn can improve the sensitivity of a pressure meter connected to the outer openings of the fluid passages to changes in the gravitational pressure head between the inner openings.

Typically, the section of conduit has a circular transverse cross-section. Preferably, the inner openings of the fluid passages are on the same transverse cross-section of the section of conduit. Preferably, the inner openings are at facing portions of the wall (i.e. on a section of conduit which has a circular transverse cross-section, the inner openings are preferably at diametrically opposing positions). Typically, the passages extend horizontally in a direction which is perpendicular to the axial direction of the section of conduit.

The conduit section may further have a pressure meter connected across the outer openings of the fluid passages for measuring a pressure difference between the inner openings.

Although in use the passages extend substantially horizontally across the wall of the conduit, each passage may extend initially from its inner opening in a direction which is perpendicular to that part of the internal face of the wall where the inner opening is located. Typically, this results in a short section of passage which is non-horizontal, or even vertical. When the section of conduit conveys a swirling flow of gas-liquid mixture, the liquid at the wall will have a substantial circumferential velocity component. However, by having the passage extend initially from the inner opening in a direction which is perpendicular to the internal face of the wall, this velocity component is prevented from forcing liquid from the swirling flow directly into the passages.

BRIEF DESCRIPTION OF THE DRAWINGS

The invention will be described by way of example with reference to the accompanying drawings, in which.

DETAILED DESCRIPTION

Figure 1:
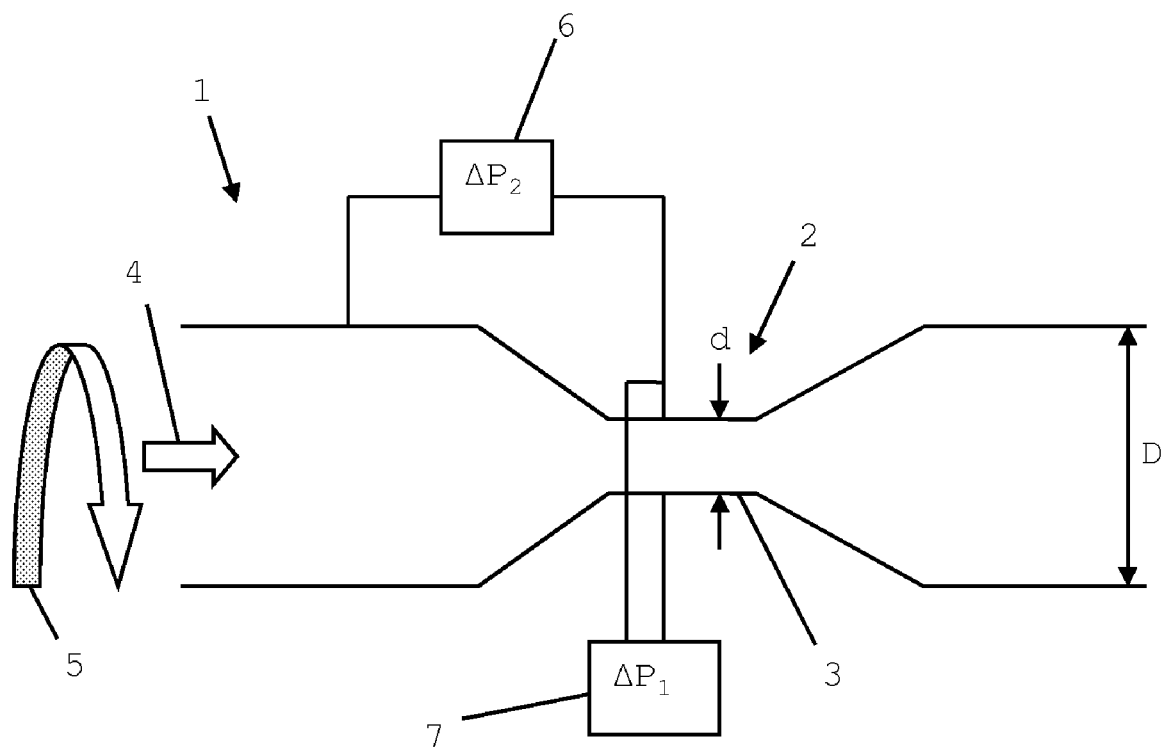
FIG. 1 shows schematically a longitudinal section through a first embodiment of an apparatus for providing measurements useable in determining a flow rate of a gas-liquid fluid mixture.

FIG. 1 shows schematically a longitudinal section through a first embodiment of an apparatus for providing measurements useable in determining a flow rate of a gas-liquid fluid mixture.

The apparatus comprises a substantially horizontal conduit 1 of circular cross-section. The conduit has a Venturi 2, the throat 3 of the Venturi providing a constriction region in the conduit.

Figure 2:
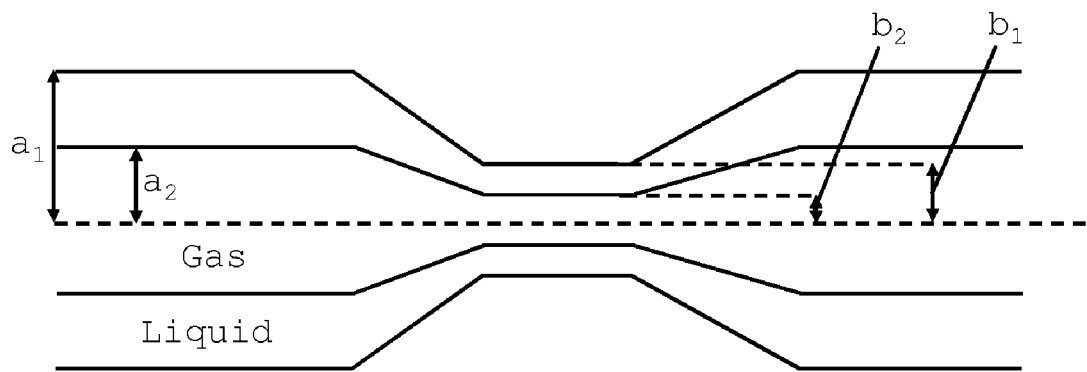
FIG. 2 shows schematically the gas and liquid distribution for the section of FIG. 1.

A gas-liquid fluid mixture flows through the conduit in the direction indicated by arrow 4. A swirl element (not shown) induces the mixture to exhibit swirling flow as indicated by arrow 5. An effect of this swirling flow is that liquid from the mixture is displaced to the wall of the conduit to form a liquid annulus around a gas core, shown schematically in FIG. 2. In the throat of the Venturi, centrifugal acceleration enhances the displacement of liquid to the wall of the conduit.

Returning to FIG. 1, on a transverse cross-section at the Venturi throat, a first pressure meter 7 measures the pressure difference, $\Delta P_1$, between facing measurement positions on upper and lower wall portions of the throat. A second pressure meter 6 measures the pressure difference, $\Delta P_2$, between a measurement position in a throat of the Venturi at the transverse cross-section for $\Delta P_1$, and a measurement position in the conduit at the inlet to the Venturi. The diameter of the conduit at the Venturi inlet cross-section containing the upstream measurement position for $\Delta P_2$ is D, and the diameter of the Venturi throat is d.

Assuming there is no slip between the liquid and gas phases, the following analysis allows the gas and the liquid flow rates to be calculated.

Notation:

q = volumetric flow rate
α = hold up
GVF = gas volume fraction
ρ = density
P = pressure
ΔP = pressure difference
v = velocity Subscripts T = total
L = liquid
G = gas
M = mixture
H = homogeneous Superscripts t = throat
i = inlet The total volumetric flow rate in the conduit is given by the Venturi equation:

$$q_T = k\sqrt{\frac{\Delta P_2}{\rho_M}}$$

where k is a constant.

Experience with the Vx™ system indicates that using the mixture density at the throat of the Venturi, $\rho_M^t$, in the above equation provides more accurate results. This density can be obtained from the pressure difference across the throat, $\Delta P_1 = f(\rho_M^t, d)$.

For example, it can be shown (see the Annex) that for swirling flow through a conduit of circular cross-section that:

$$\Delta P_1 = \rho_M^t dg$$

where g is acceleration due to gravity.

Thus the Venturi equation can be rewritten as:

$$q_T^t = k\sqrt{\frac{\Delta P_2}{\rho_M^t f(\Delta P_1, d)}}$$

The liquid and gas densities, $\rho_L$ and $\rho_G$, are generally known at line conditions or can be estimated. For example, at typical line conditions of a mixture of natural gas and condensate, $\rho_L$ is effectively a constant, and $\rho_G$ varies in a known way (i.e. according to the ideal gas law) with pressure and temperature. If the pressure and/or temperature in the conduit are not known, they can be measured by suitable devices. For example, pressure meter 7 may incorporate a device for measuring the absolute pressure in the conduit at the throat, $P^t$. A further device (not shown) may be provided for measuring the temperature at that position.

Under the no slip assumption, the liquid and gas densities allow the gas hold up, $\alpha_G$, to be determined from the expression:

$$\rho_M = \alpha_G \rho_G + (1 - \alpha_G) \rho_L$$

which can be rearranged as:

$$\alpha_G = \frac{\rho_L - \rho_M}{\rho_L - \rho_G}$$

whereby:

$$q_G{}^t = q_T{}^t \alpha_G{}^t$$

$$q_L{}^t = q_T{}^t - q_G{}^t$$

Thus the volumetric flow rates of the gas and liquid in the throat can be calculated from knowledge of the liquid and gas densities in the throat, and from the measurements $\Delta P_1$ and $\Delta P_2$. Evidently, these volumetric flow rates can be converted into mass flow rates, or into volumetric flow rates at other positions in the conduit (e.g. applying the ideal gas law, but ignoring the effect of temperature which will be small, $q_G{}^i$ can be calculated from the expression $q_G{}^i = q_G{}^t(P^t/(P^t + \Delta P_2))$).

Similar analyses can be performed for types of flow other than swirling flow, but in such analyses the constant k in the Venturi equation and the expression relating $\Delta P_1$ to the mixture density may be different.

Figure 3:
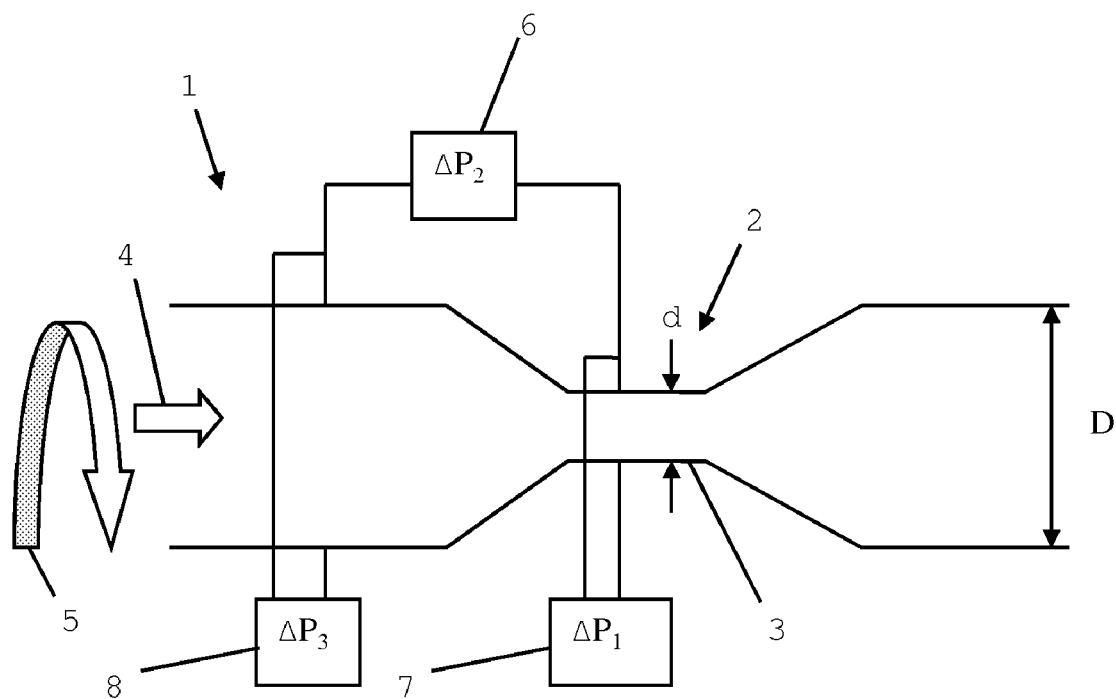
FIG. 3 shows schematically a longitudinal section through a second embodiment of an apparatus for providing measurements useable in determining a flow rate of a gas-liquid fluid mixture.

FIG. 3 shows schematically a longitudinal section through a second embodiment of an apparatus for providing measurements useable in determining a flow rate of a gas-liquid fluid mixture. The apparatus is similar to the apparatus of the first embodiment, and the same numbers are used in FIGS. 1 and 3 for common features of the two embodiments. However, the second embodiment differs from the first embodiment in that on the inlet transverse cross-section containing the upstream measurement position for $\Delta P_2$, a third pressure meter 8 measures the pressure difference, $\Delta P_3$, between facing positions on upper and lower wall portions of the conduit.

The following analysis allows the gas and the liquid flow rates to be calculated, with the additional pressure difference, $\Delta P_3$, enabling slip between the gas and liquid phases to be accounted for. As in the previous analysis, it assumes that $\rho_L$ is a known constant, and $\rho_G$ varies in a known way with pressure and temperature.

The pressure differences $\Delta P_1$ and $\Delta P_3$ are related to the densities of the fluid mixture at respectively the inlet to the Venturi and the throat, i.e. $\Delta P_3 = f(\rho_M{}^i, D)$ and $\Delta P_1 = f(\rho_M{}^t, d)$.

Thus, as in the previous analysis, the Venturi equation can be rewritten as:

$$q_T^t = k\sqrt{\frac{\Delta P_2}{\rho_M^t f(\Delta P_1, d)}} \qquad \text{Equation (1)}$$

Further, the respective gas hold ups at the inlet to the Venturi and the throat can be determined from:

$$\alpha_G^i = \frac{(\rho_L - \rho_M^i)}{(\rho_L - \rho_G^i)} \qquad \text{Equation (2)}$$

$$\alpha_G^t = \frac{(\rho_L - \rho_M^t)}{(\rho_L - \rho_G^t)}$$

whereby the change in gas hold up from the inlet to the throat of the Venturi can be calculated:

$$\Delta \alpha_G = \alpha_G^t - \alpha_G^i \qquad \text{Equation (3)}$$

Next, we seek an expression for the change in GVF from the inlet to the throat of the Venturi. Firstly, applying the ideal gas law:

$$q_G^t = q_G^i \frac{P^i}{P^t} \frac{T^t}{T^i}$$

Because typical variations in absolute temperature are small, the $T^t/T^i$ term will be close to unity and can be disregarded. Conveniently, pressure meters 7, 8 incorporate devices to measure $P^i$ and $P^t$ as well as $\Delta P_1$ and $\Delta P_3$. Thus the change in gas flow rate from the inlet to the throat of the Venturi can be expressed as:

$$\Delta q_G = q_G^t - q_G^i = q_G^t \left(1 - \frac{P^t}{P^i}\right)$$

Now, $\text{GVF} = q_G/(q_G + q_L)$, whereby, on the reasonable assumption that $q_L$ is invariant:

$$\frac{\Delta GVF}{\Delta q_G} = \frac{q_L}{(q_G + q_L)^2} = \frac{q_L}{q_T^2} \qquad \text{Equation (4)}$$

Thus:

$$\Delta GVF = \frac{q_L}{q_T^2} \cdot q_G^t \left(1 - \frac{P^t}{P^i}\right)$$

Slip can be expressed in the relation between GVF and $\alpha_G$. That is:

$$GVF = \frac{q_G}{q_T} = \alpha_G \frac{v_G}{v_H}$$

Figure 4:
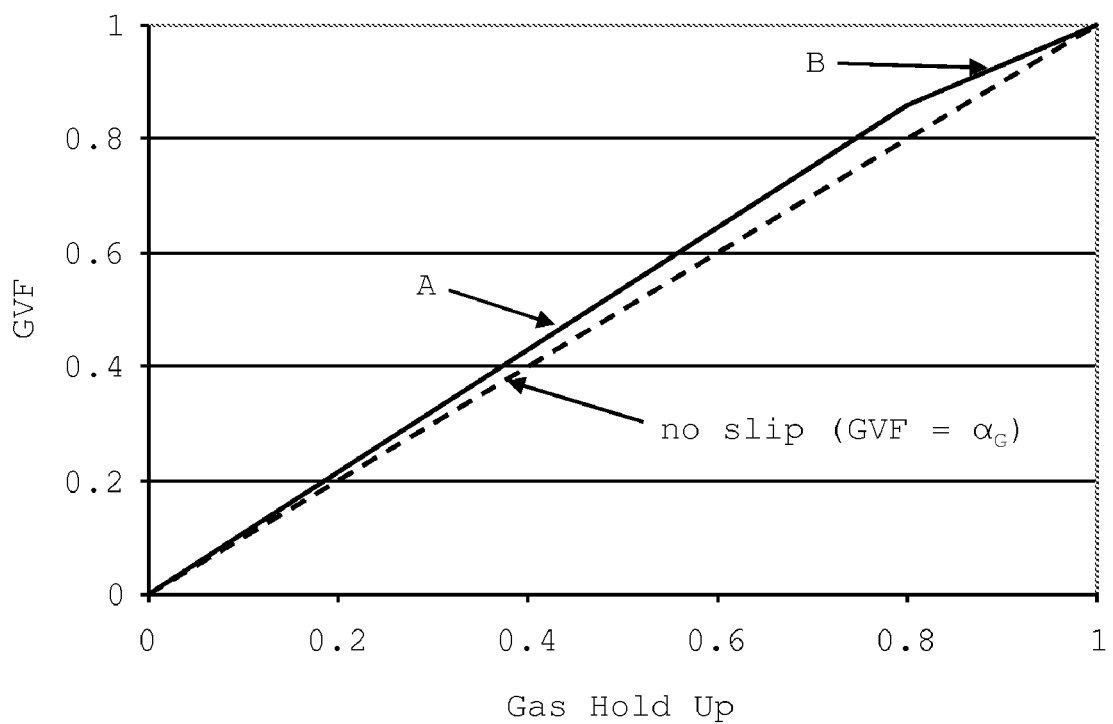
FIG. 4 is a plot of gas volume fraction against gas hold up.

In general, where there is slip, $\text{GVF} \geq \alpha_G$, although when there is single phase flow $\text{GVF} = \alpha_G = 1$ and $\text{GVF} = \alpha_G = 0$. Thus, as shown in FIG. 4, the slip law can be approximated by two straight lines A and B representing a deviation from a situation where there is no slip (i.e. $\text{GVF} = \alpha_G$).

For line A:

$$\frac{\Delta GVF}{\Delta \alpha_G} \geq 1, \text{ and } GVF = 0 \text{ when } \alpha_G = 0$$

$$\Rightarrow GVF = \frac{\Delta GVF}{\Delta \alpha_G} \alpha_G$$

while for line B:

$$\frac{\Delta GVF}{\Delta \alpha_G} < 1, \text{ and } GVF = 1 \text{ when } \alpha_G = 1$$

$$\Rightarrow GVF = \frac{\Delta GVF}{\Delta \alpha_G}(\alpha_G - 1) + 1$$

Applying this slip law, it is then possible to iteratively determine the GVF and hence to calculate the gas and liquid flow rates. The steps of the iteration are as follows:

1) Determine $q_T^t$ from Equation (1)
2) Determine $\alpha_G^t$ from Equation (2)
3) Determine $\Delta \alpha_G$ from Equation (3)
4) Assuming no slip, set $\text{GVF}^t = \alpha_G^t$ 5) $q_G{}^t = GVF^{t'} \cdot q_T{}^t \quad q_L = q_T{}^t - q_G{}^t$ 6) Determine $\Delta GVF$ from Equation (4)

7) Calculate $$\frac{\Delta GVF}{\Delta \alpha_G}$$

8) If $$\frac{\Delta GVF}{\Delta \alpha_G} \geq 1$$

then reset $$GVF^t = \frac{\Delta GVF}{\Delta \alpha_G} \alpha_G^t$$

(slip law line A), whereas if $$\frac{\Delta GVF}{\Delta \alpha_G} < 1$$

then reset $$GVF^t = \frac{\Delta GVF}{\Delta \alpha_G}(\alpha_G^t - 1) + 1$$

(slip law line B)

9) Iterate around 5) to 8) until $GVF^t$ has converged

10) $q_G{}^t = GVF^{t'} \cdot q_T{}^t \quad q_L = q_T{}^t - q_G{}^t$

Again, these volumetric flow rates can be converted into mass flow rates, or into volumetric flow rates at other positions in the conduit.

The analyses described above in relation to both the first and second embodiments can be performed by a suitably arranged processor (not shown in FIGS. 1 and 3) which receives the pressure difference measurements from the pressure meters of the respective apparatus (and optionally receives absolute pressure and temperature measurements). The flow rate calculations resulting from the analyses can be then be transmitted, stored and/or displayed. Because the swirling flow may not be steady, and to reduce the effect of noise in the pressure difference measurements, it can be advantageous for the analyses to be performed on time-averaged pressure difference measurements.

Although the pressure differences $\Delta P_1$ and $\Delta P_3$ will generally be small, it is possible to measure the differences with enough accuracy. For example, putting approximate values of d=0.1 m and g=10 m s$^{-2}$ into the expression $\Delta P_1 = \rho_M{}^t dg$, and assuming a maximum value for $\rho_M{}^t = 1000$ kg m$^{-3}$, gives an approximate upper value for $\Delta P_1 = 1000$ Pa. Honeywell's ST 3000™ Series 100 differential pressure meter model STD120 is an example of a conventional pressure meter that could be used to measure $\Delta P_1$ and $\Delta P_3$. This meter should have a sufficient accuracy of about ±1 Pa over the span 0 to 1000 Pa.

Indeed, because the $\Delta P_1$ term in the Venturi equation (Equation (1) above), appears in a square root, the impact of errors in the measurement of $\Delta P_1$ on the calculated flow rates is reduced.

Figure 5:
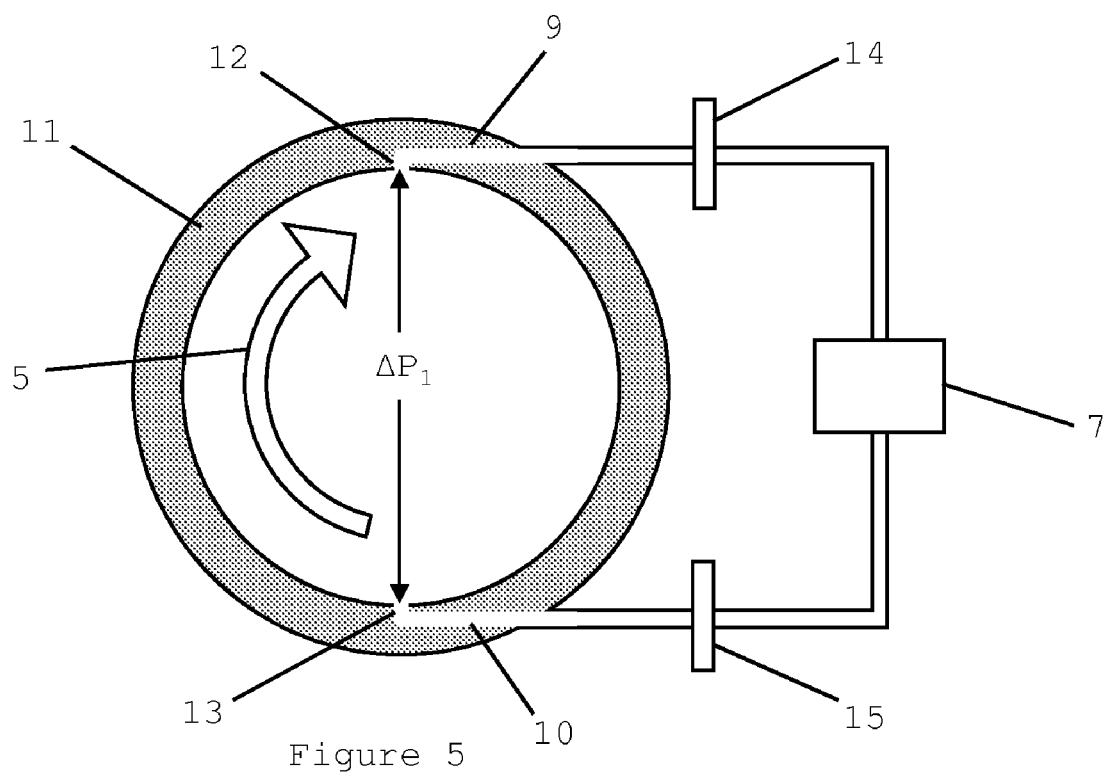
FIG. 5 is a schematic transverse cross-section of the conduit of FIG. 1 or 3 at the measurement positions for $\Delta P_1$.
Figure 6:
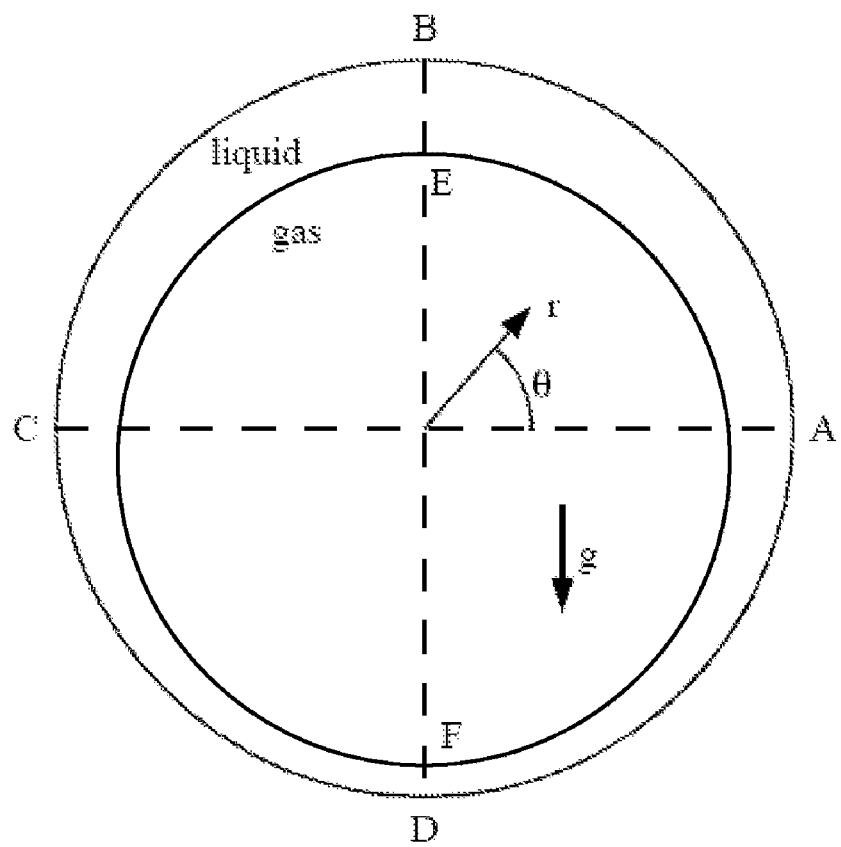
FIG. 6 shows a schematic transverse cross-section through the apparatus of either FIG. 1 or 3.

Precautions can also be taken to improve the accuracy of the $\Delta P_1$ and $\Delta P_3$ measurements. For example, as shown in FIG. 5, which is a schematic transverse cross-section of the conduit of FIG. 1 or 3 at the measurement positions for $\Delta P_1$, fluid-filled passages 9, 10 connecting to pressure meter 7 extend substantially horizontally through the wall 11 of the conduit. By avoiding unnecessary fluid columns above and below the locations where the passages open into the conduit at facing upper and lower wall portions, the sensitivity of the pressure meter to changes in the gravitational pressure head between the passages openings is improved. Nonetheless, the passages do have short vertical sections 12, 13 adjacent the openings into the conduit. These short sections help to prevent liquid from the swirling flow 5 being forced into the passages by the circumferential velocity component of the flow. Preferably, pressure meter 7 is isolated from the conduit fluid by isolation bellows 14, 15 in passages 9, 10. Suitable bellows are available from e.g. Honeywell in their ST 3000™ Series 100.

While the invention has been described in conjunction with the exemplary embodiments described above, many equivalent modifications and variations will be apparent to those skilled in the art when given this disclosure. Accordingly, the exemplary embodiments of the invention set forth above are considered to be illustrative and not limiting. Various changes to the described embodiments may be made without departing from the scope of the invention.

The invention claimed is:

1. A method for measuring a flow rate of a gas-liquid fluid mixture, comprising the steps of:
   providing a conduit through which the gas-liquid fluid mixture flows, the conduit extending substantially horizontally and having a constriction region having a reduced conduit cross-section;
   conditioning the fluid mixture to exhibit swirling flow in the conduit, wherein the swirling flow separates the liquid from the gas;
   measuring a first pressure difference between two vertically-spaced measurement positions in the conduit;
   measuring a second pressure difference between two horizontally-spaced measurement positions in the conduit, the first horizontally-spaced measurement position being at the constriction region and the second horizontally-spaced measurement position being upstream or downstream of the constriction region; and
   using the first and the second pressure differences to determine a flow rate of the gas-liquid fluid mixture.

2. A method according to claim 1, wherein the second horizontally-spaced measurement position is upstream of the constriction region.

3. A method according to claim 1, wherein the constriction region is provided by a Venturi.

4. A method according to claim 3, wherein the constriction region is the throat of the Venturi.

5. A method according to claim 3, wherein the second horizontally-spaced measurement position is at the inlet to the Venturi.

6. A method according to claim 1, further comprising the step of measuring a third pressure difference between two further vertically-spaced measurement positions in the conduit spaced upstream or downstream of the vertically-spaced measurement positions where the first pressure difference is measured;
   wherein the first, second and third pressure differences are used to determine said flow rate.

7. A method according to claim 1, wherein the fluid mixture comprises natural gas and condensate.

8. An apparatus for providing measurements useable in determining a flow rate of a gas-liquid fluid mixture, the apparatus comprising:
- a conduit through which the gas-liquid fluid mixture can flow, the conduit extending substantially horizontally and having a constriction region having a reduced conduit cross-section;
- a first pressure meter for measuring a first pressure difference between two vertically-spaced measurement positions in the conduit;
- a second pressure meter for measuring a second pressure difference between two horizontally-spaced measurement positions in the conduit, the first horizontally-spaced measurement position being at the constriction region and the second horizontally-spaced measurement position being upstream or downstream of the constriction region; and
- a swirl element for inducing the fluid mixture to exhibit swirling flow at the measurement positions; wherein the first and the second pressure differences are usable to determine a flow rate of the gas-liquid fluid mixture.

9. An apparatus according to claim 8, wherein the second horizontally-spaced measurement position is upstream of the constriction region.

10. An apparatus according to claim 8, wherein the constriction region is provided by a Venturi.

11. An apparatus according to claim 10, wherein the constriction region is the throat of the Venturi.

12. An apparatus according to claim 10, wherein the second horizontally-spaced measurement position is at the inlet to the Venturi.

13. An apparatus according to claim 8, further comprising a third pressure meter for measuring a third pressure difference between two further vertically-spaced measurement positions in the conduit spaced upstream or downstream of the vertically-spaced measurement positions where the first pressure difference is measured.

14. A meter comprising the apparatus of claim 8, wherein a processor is arranged to determine a density of the fluid using the pressure difference measured by the pressure meter of the apparatus.

15. A flow meter comprising the apparatus of claim 8, wherein a processor is arranged to determine a flow rate of the gas-liquid fluid mixture using the pressure differences measured by the pressure meters of the apparatus.

16. An oil well pipeline or a gas well pipeline comprising an apparatus according to claim 8.

17. An oil well pipeline or a gas well pipeline comprising a meter according to claim 15.

18. An apparatus for providing measurements useable in determining a flow rate of a gas-liquid fluid mixture, the apparatus comprising:
- a section of conduit, wherein the section of conduit includes a constriction region having a reduced conduit cross-section, and wherein the section of conduit comprises a conduit wall;
- an upper fluid passage traversing the conduit wall;
- a lower fluid passage traversing the conduit wall, wherein each of the fluid passages extend between an inner opening on the internal face of the conduit wall and an outer opening on the external face of the conduit wall where each passage extends initially from its inner opening in a direction which is perpendicular to that part of the internal face of the conduit wall where the inner opening is located, and wherein the passages are arranged such that, when the section of conduit is viewed along its axial direction with the inner opening of the upper passage directly above the inner opening of the lower passage, the passages extend substantially horizontally between their respective inner and outer openings;
- a first pressure meter connected across the outer openings of the fluid passages for measuring a pressure difference between the inner openings; and
- a second pressure meter configured for measuring a pressure difference between two horizontally-spaced measurement positions in the conduit, the first horizontally-spaced measurement position being at the constriction region and the second horizontally-spaced measurement position being upstream or downstream of the constriction region.

* * * * *